(12) United States Patent
Suzuki et al.

(10) Patent No.: US 7,553,301 B2
(45) Date of Patent: Jun. 30, 2009

(54) METHOD FOR DETERMINING THE ILLUSTRATION OF A DIAPER

(75) Inventors: Sachiyo Suzuki, Kagawa (JP); Hiroki Ishikawa, Kagawa (JP); Satoru Sakaguchi, Kagawa (JP); Kaori Yuasa, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 516 days.

(21) Appl. No.: 10/878,670

(22) Filed: Jun. 29, 2004

(65) Prior Publication Data

US 2005/0059943 A1 Mar. 17, 2005

Related U.S. Application Data

(63) Continuation of application No. PCT/JP03/11243, filed on Sep. 3, 2003.

(51) Int. Cl.
*A61F 13/15* (2006.01)
*G06F 7/00* (2006.01)

(52) U.S. Cl. .................. 604/385.01; 604/361; 604/358; 707/102

(58) Field of Classification Search .................. 604/361, 604/358, 385.01, 362; 707/102; 600/549
See application file for complete search history.

(56) References Cited

U.S. PATENT DOCUMENTS 6,297,424 B1 * 10/2001 Olson et al. .................. 604/361

2003/0114808 A1 * 6/2003 Underhill et al. ............ 604/361

FOREIGN PATENT DOCUMENTS

| JP | U-62-129005 | 8/1987 |
|---|---|---|
| JP | A-5-247701 | 9/1993 |
| JP | A-2000-27009 | 1/2000 |
| JP | A-2001-73201 | 3/2001 |
| JP | A-2002-95696 | 4/2002 |
| WO | 0076439 A2 | 12/2000 |
| WO | WO 01-49230 | 7/2001 |

OTHER PUBLICATIONS

Notice of Reasons for Rejection of Japanese Patent Application No. 2002-307685 mailed Nov. 25, 2008.

* cited by examiner

*Primary Examiner*—Jacqueline F. Stephens
(74) *Attorney, Agent, or Firm*—Lowe Hauptman Ham & Berner, LLP

(57) ABSTRACT

The present invention relates to a method for determining illustrations for a diaper to be worn, for example, by an infant. With the present invention's illustration determination method, for a diaper, comprising a main body, fitted onto the body of an infant, and an illustration displaying part, provided on the main body for displaying an illustration, the above-mentioned illustration is determined based on the age in months of the infant. The illustration can arouse interest of an infant definitely since the object of interest of an infant depends on his/her age in months. An infant can thus be made to calm down during diaper exchange and the labor of diaper exchange can be alleviated.

4 Claims, 6 Drawing Sheets

23A

24A

23B

24B

23C

24C

US 7,553,301 B2

METHOD FOR DETERMINING THE ILLUSTRATION OF A DIAPER

CROSS-REFERENCE TO RELATED APPLICATIONS

This application is a Continuation of International Application No. PCT/JP2003/011243 filed Sep. 3, 2003, which application published in Japanese on Mar. 25, 2004 as WO 2004/024049 A2 under PCT Article 21 (2). The International Application PCT/JP2003/011243 is based upon and claims the benefit of priority from Japanese Patent application No.2002-307685 filed on Sep. 13, 2002, the entire contents of which is incorporated herein by reference.

BACKGROUND OF THE INVENTION

1. Technical Field

The present invention relates to a method for determining an illustration to be displayed on a diaper worn by an infant.

2. Background Art

Conventionally, infants wear diapers since they cannot control their excretion at their own will. However in some cases, an infant dislikes the exchange of a diaper and struggles, and thus the exchange of a diaper has been burdensome, both physically and mentally, for a mother or other diaper exchanger.

Thus in order to alleviate such a burden, a diaper, provided with an illustration of a cute character, etc. that is considered to make infants happy, has been proposed (see for example, International Patent Publication No. 01/49230 Pamphlet).

With the present invention, a diaper is provided with an illustration and the light transmittance of a nonwoven fabric that forms the diaper is made 80% or more so as not to lower the impact of the illustration. An infant can thereby be pleased and the infant's will for diaper exchange can be increased.

However, the abovementioned diaper cannot arouse interest of an infant and, actually infants who can perform movements of the hands and feet, such as crawling, grab-walking, etc., dislike diaper exchange and escape or struggle, and thus the burden of diaper exchange that is placed on an exchanger was not alleviated.

DISCLOSURE OF THE INVENTION

The present invention has been made in view of problems such as the above and an object thereof is to provide a method for determining illustrations for a diaper which can arouse interest of an infant and alleviate the labor of a diaper exchanger in the process of diaper exchange.

In order to achieve the above object, the present Applicant noted that improvement of the quality of communication between a diaper exchanger (mainly a mother) and an infant during a diaper exchange process is important for lightening of the physical and mental burdens of the exchanger in the diaper exchanging process and promotion of healthy growth of the infant.

Here it is known that in general, the visual acuity of an infant is only approximately 0.04 to 0.08 at 6 months of age, 0.2 to 0.25 at 12 months of age, and 0.5 to 0.6 at 24 months of age and that differences of character figures can be distinguished only past 1 year of age. It has also become clear from an Applicant's and other's own study that "an infant of 6 months to 17 months shows an interest in rattles, suspended merry-go-rounds, and other toys that make sounds or move, and an infant of 18 months to 24 months show an interest in a simple story development, such as peek-a-boo."

Based on the above facts, the present Applicant analyzed the various behavior patterns of infants in a diaper exchange process. As a result of this Applicant's research, it has become clear that an infant shows more interest in drastic changes among illustrations rather than in diverse types of illustrations. The present Applicant thus found a solution concerning the diaper exchange of infants and has come to complete the present invention.

More specifically, the present invention provides the following:

(1) A method for determining an illustration for a diaper, comprising a main body, for being fitted onto a body of an infant, and a first illustration displaying part, provided on the main body, for displaying a first illustration, wherein said illustration is determined based on the age in months of the infant.

With the present invention, the illustration of the illustration displaying part is determined in accordance with the age in months of an infant. The illustration can arouse interest of an infant definitely since the object of interest of an infant depends on his/her age in months. An infant can thus be made to calm down during diaper exchange and the labor of diaper exchange can be alleviated.

(2) The above-described method for determining an illustration for a diaper, further comprising a second illustration display part for displaying a second illustration, wherein said first illustration and said second illustration are mutually relevant or integrated as a whole in terms of shape, pattern, color, concept, or combination thereof.

With the present invention, for example, different illustrations can be shown in order to an infant. An infant can thereby be made to recognize changes in the illustrations and these changes in the illustrations can arouse interest of the infant definitely. The labor of a diaper exchanger in the diaper exchanging process can thus be alleviated.

(3) The above-described method for determining an illustration for a diaper, wherein said diaper is disposable in a state in which it retains the excrement of the infant.

(4) The above-described method for determining an illustration for a diaper, wherein at least one specific character is included in said illustration.

(5) The above-described method for determining an illustration for a diaper, wherein said age in months is 36 months or less.

(6) The above-described method for determining an illustration for a diaper, wherein said age in months is 12 months or more and less than 24 months.

(7) The above-described method for determining an illustration for a diaper, wherein said age in months is 18 months or more and less than 24 months.

(8) The above-described method for determining an illustration for a diaper, wherein said main body is provided with fixing tape and by rounding up said diaper and fixing the end of the fixing tape to the surface of said main body, the fixing tape is made to hold said diaper in a rounded state.

(9) The above-described method for determining an illustration for a diaper, wherein said main body has the shape of pants.

(10) The above-described method for determining an illustration for a diaper, wherein said illustration is selected from a plurality of illustrations on the basis of an approach value, which is the total amount of time when a diaper exchanger approaches the infant for conveying will in a period from the start of exchange of the diaper to the completion of exchange.

(11) The above-described method for determining an illustration for a diaper, wherein said illustration is selected from a plurality of illustrations on the basis of the sum of an approach value, which is the total amount of time when a diaper exchanger approaches the infant for conveying will in a period from the start of exchange of the diaper to the completion of exchange, and a positive response value, which is the total amount of time when the infant expresses a positive emotion to an approach of the diaper exchanger.

(12) The above-described method for determining an illustration for a diaper, wherein said illustration is selected from a plurality of illustrations on the basis of the sum of a positive response value, which is the total amount of time when the infant expresses a positive emotion to an approach of the diaper exchanger to convey will to the infant, and a negative response value, which is the total amount of time when the infant expresses a negative emotion to the approach of the diaper exchanger to convey will to the infant in a period from the start of exchange of the diaper to the completion of exchange.

(13) A method for exchanging a diaper, comprising a main body, fitted onto the body of an infant, and illustration displaying parts, provided on this main body and displaying illustrations, wherein said diaper is exchanged by showing to the infant one of the illustrations displayed on the illustration displaying parts and thereafter changing the position of said main body and showing another of the illustrations to the infant.

With the present invention, for example, different illustrations can be shown in order to an infant. An infant can thereby be made to recognize changes in the illustrations and these changes in the illustrations can arouse interest of the infant. The labor of a diaper exchanger in the diaper exchanging process can thus be alleviated.

PREFERRED EMBODIMENTS OF THE INVENTION

An embodiment of the present invention shall now be described based on the drawings.

Figure 1:
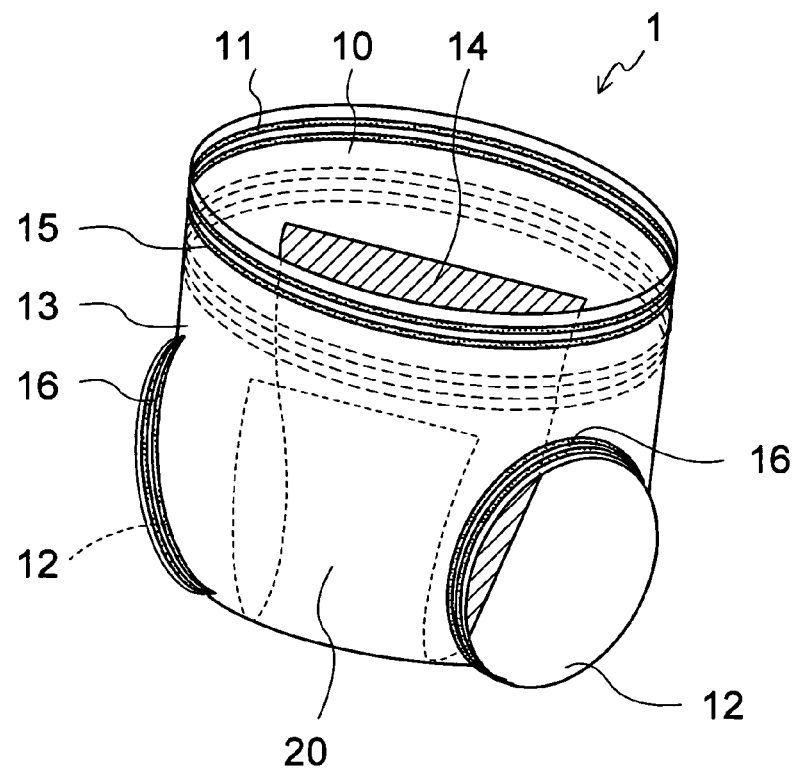
FIG. 1 is an overall perspective view of a diaper according to an embodiment of the present invention.

FIG. 1 shows a diaper 1 according to a first embodiment of the present invention.

Diaper 1 is worn by an infant and comprises a foldable main body 10, which is fitted onto the body of an infant, and an illustration displaying part 20, which is provided on this main body 10 and displays illustrations.

Main body 10 has the shape of pants and comprises an outer part 13, having a waist opening 11 fitted to the trunk of an infant and two leg openings 12 fitted to the legs of the infant, and an inner part 14, which extends from the front side to the rear side of waist opening 11 via the part between leg openings 12 at the inner side of outer part 13. This main body 10 can be turned over and thereby changed in position.

In order to secure resistance against fluid, good touch to skin, and air permeability, outer part 13 is arranged from a plurality of sheets. For example, hydrophobic nonwoven fabrics, non-water-permeating plastic films, or sheets formed by laminating such fabrics or films may be used as these sheets. With a plastic film, air permeability and moisture permeability can be secured by stretching after mixing in a filler.

Outer part 13 is provided with a waist tightening part 15 and leg tightening parts 16 along waist opening 11 and leg openings 12. Each of these tightening parts 15, 16 is formed by providing an elastic member between a plurality of sheets that make up outer part 13. Here, as the elastic member, a plastic sheet made of natural rubber, synthetic rubber, or thermoplastic synthetic resin may be used. This elastic member is, for example, put in a stretched state and then sandwiched between two sheets and bonded by hot melting.

Inner part 14 comprises an absorbent member provided on outer part 13 and a top sheet that covers the absorbent member. The absorbent member is formed of hydrophilic fibers and a highly absorbing polymer. As the hydrophilic fibers, absorbent fibers, such as pulp, rayon, acetate, cotton, etc., fibers prepared by hydrophilization of synthetic thermoplastic resin fibers, etc., are used. A plastic film may also be provided to retain body fluids excreted by an infant.

A hydrophilic nonwoven fabric or a liquid-permeating sheet of porous plastic, etc. is used as the top sheet. The nonwoven fabric is manufactured by a method such span lacing, needle punching, melt blowing, thermal bonding, chemical bonding, air-through method, etc. As the fibers of the nonwoven fabric, polyolefin-, polyester-, or polyamide-based fibers or sheath-core type composite fibers or side-by-side fibers formed of polyethylene, polypropylene, or ester may be used.

The above-described inner part 14 is bonded to outer part 13 using heat sealing, ultrasonic sealing, hot-melt adhesive, etc.

Figure 2:
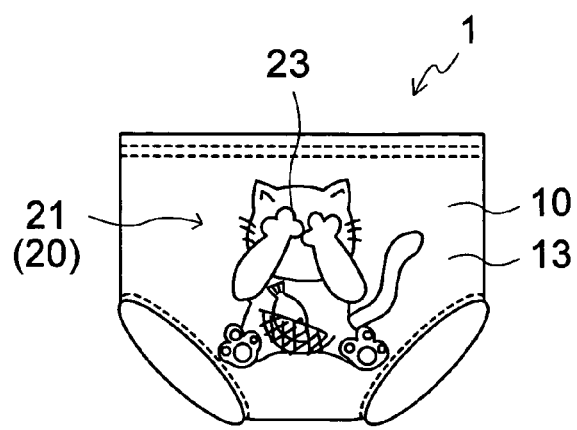
FIG. 2A is a front view of the diaper according to the abovementioned embodiment.
FIG. 2B is a rear view of the diaper according to the abovementioned embodiment.
Figure 2:
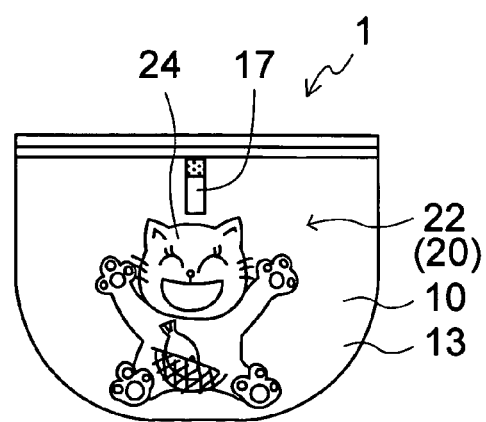

Illustration displaying part 20 has a first illustration displaying part 21, which, as shown in FIG. 2A, is positioned at the front surface of main body 10, and a second illustration displaying part 22, which, as shown in FIG. 2B, is positioned at the rear surface of main body 10.

First illustration display part 21 displays, as a first illustration 23, a state in which a cat (character) hides its face. Second illustration display part 22 displays, as a second illustration 24, a state in which the cat shows its face. First illustration 23 and second illustration 24 express the hiding and showing of the face by the cat, that is, a behavior of a character and are mutually related in terms of coloration.

As long as the respective illustration displaying parts 21, 22 are provided at locations that can be visually recognized from the outer side of diaper 1, the arrangement thereof is not limited in particular. For example, illustrations may be printed directly, or illustrations may be printed on films and thereafter the films may be adhered onto the nonwoven fabric or film that makes up outer part 13.

Thus in a state where an infant can visually recognize the front surface of diaper 1, the state in which the cat hides its face is shown to the infant by illustration first displaying part 21. In a state where an infant can visually recognize the rear surface of diaper 1, the state in which the cat shows its face is shown to the infant by second illustration displaying part 22.

Thus by simply turning over diaper 1, a diaper exchanger can show to the infant the behavior of a cat showing its face from a state in which it hides its face.

As shown in FIG. 2A, at the rear surface side of waist opening 11 of outer part 13 is provided a fixing tape 17 for holding diaper 1 in a rounded state. Fixing tape 17 has an adhesive part and a holding part, which is provided integrally at the tip of the adhesive part. This adhesive part is formed by coating an adhesive agent onto a plastic film.

Figure 3:
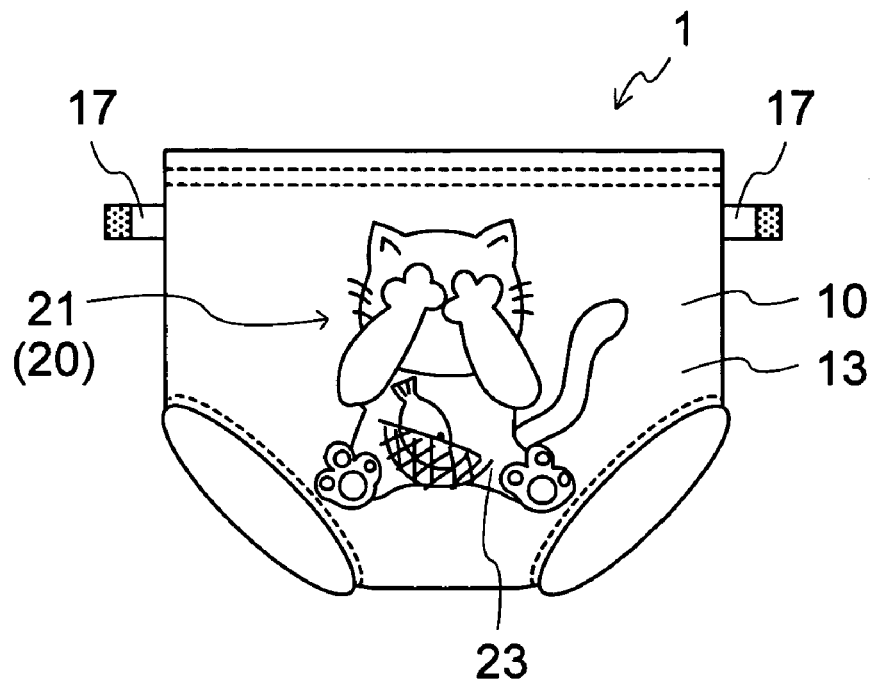
FIG. 3 is a front view of a diaper according to a first modification example of the present invention.
Figure 4:
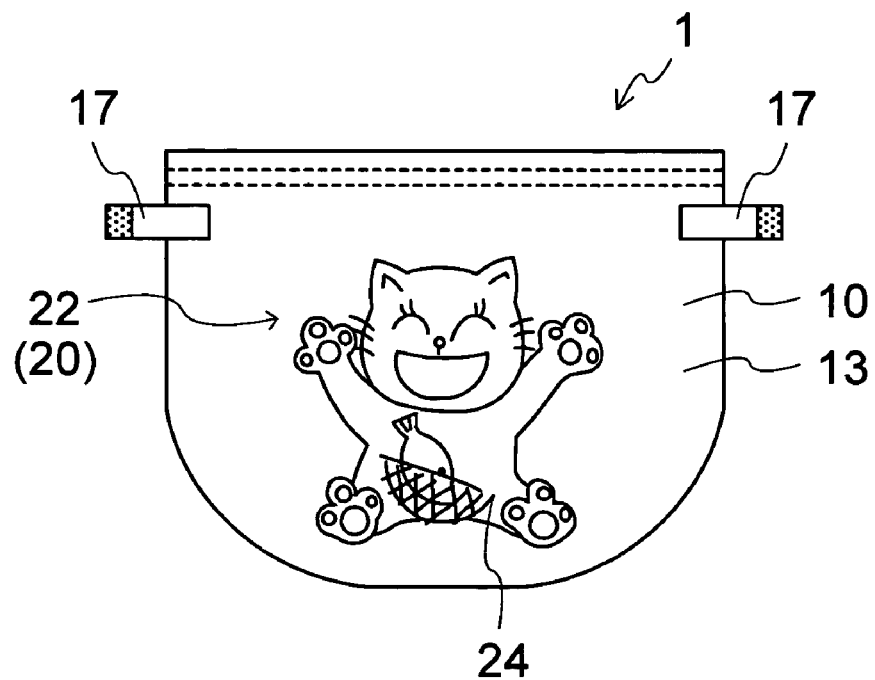
FIG. 4 is a rear view of a diaper according to a second modification example of the present invention.

Diaper 1 is rounded up, the holding part of fixing tape 17 is held, and the adhesive part of fixing tape 17 is adhered onto the outer surface of outer part 13. Diaper 1 can thus be kept in the rounded state. This fixing tape 17 may be folded in a Z-shaped manner or may be formed from a material with stretch ability. Also, the number of fixing tape 17 is not restricted in particular and a plurality thereof may be provided as shown in FIGS. 3 and 4.

This fixing tape 17 is arranged so as not to overlap with first illustration 23 and second illustration 24 when the adhesive part is adhered onto the outer surface of outer part 13. The fixing tape may be made transparent so that it does not hide first illustration 23 and second illustration 24 even if it overlaps with these illustrations 23 and 24.

Here, the character (cat) displayed in illustrations 23 and 24 has a size of 8 cm×8 cm. Also, one or more colors, with a hue such that the absolute value of A or B of the LAB color space of JISZ8729 is 20 or more, are used. This is because for an infant of an age in months that is targeted for use of the diaper (less than 36 months); the visual acuity is approximately 0.04 to 0.08 at 6 months, 0.2 to 0.25 at 12 months, and 0.5 to 0.6 at 24 months, and thus if an illustration is smaller than 8 cm×8 cm or the hue is low, such an infant will not recognize the illustration even if a diaper exchanger shows diaper 1 to the infant.

Though with the present embodiment, a change in the behavior of a cat (character) is expressed by first illustration displaying part 21 and second illustration displaying part 22, the present invention is not limited thereto.

Figure 5:
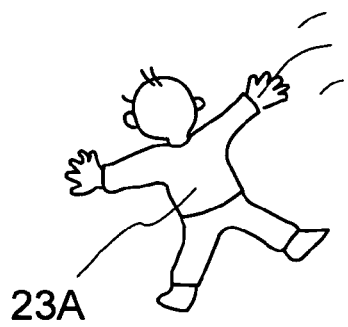
FIG. 5A is a diagram showing a first illustration of a diaper according to a third modification example of the present invention.
FIG. 5B is a diagram showing a second illustration of the diaper according to the abovementioned modification example.
Figure 5:
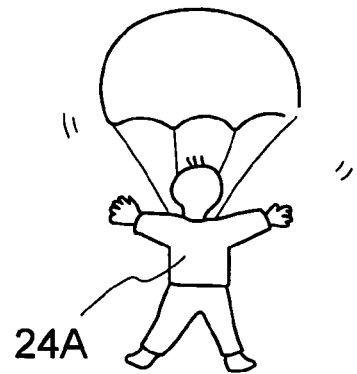

For example, a behavior and an irreversible transition in time may be expressed. To be specific, a first illustration 23A may be of a person who jumps out into air (FIG. 5A) and a second illustration 24A may be of the person with a parachute on the shoulder opening up and descending to the ground by parachute (FIG. 5B).

Figure 6:
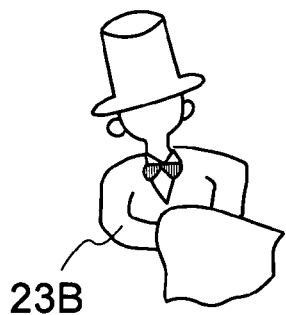
FIG. 6A is a diagram showing a first illustration of a diaper according to a fourth modification example of the present invention.
FIG. 6B is a diagram showing a second illustration of the diaper according to the abovementioned modification example.
Figure 6:
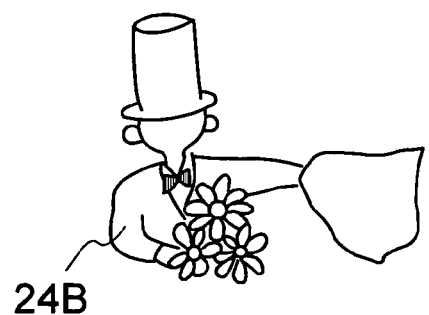

Or a change near the hands of a character may be expressed. To be specific, a first illustration 23B may be of a person (character) who hides his/her hands with a white cloth (FIG. 6A) and a second illustration 24B may be of the person who removes the white cloth and holds a bunch of flowers in his/her hands (FIG. 6B).

Figure 7:
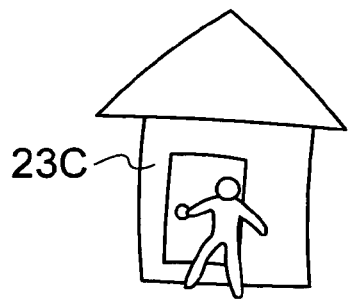
FIG. 7A is a diagram showing a first illustration of a diaper according to a fifth modification example of the present invention.
FIG. 7B is a diagram showing a second illustration of the diaper according to the abovementioned modification example.
Figure 7:
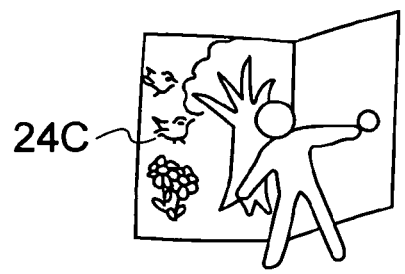

A change of scene may also be expressed. To be specific, a first illustration 23C may be that of a scene in which a person stands in front of the door of a house (FIG. 7A) and a second illustration 24C may be of a scene where a forest comes to view as the person opens the door (FIG. 7B).

Figure 8:
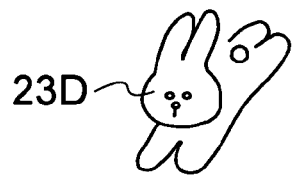
FIG. 8A is a diagram showing a first illustration of a diaper according to a sixth modification example of the present invention.
FIG. 8B is a diagram showing a second illustration of the diaper according to the abovementioned modification example.
Figure 8:
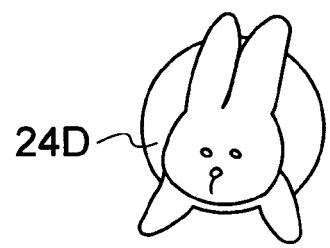

Also, a movement of a character may be expressed. To be specific, a first illustration 23D may be that of a running rabbit (character) (FIG. 8A) and a second illustration 24D may be that of the rabbit facing this way upon running through a hole in a wall (FIG. 8B).

Figure 9:
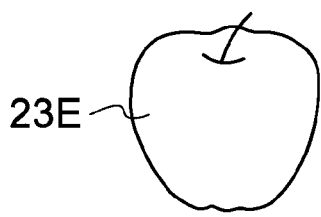
FIG. 9A is a diagram showing a first illustration of a diaper according to a seventh modification example of the present invention.
FIG. 9B is a diagram showing a second illustration of the diaper according to the abovementioned modification example.
Figure 9:

An irreversible transition in time may also be expressed. To be specific, a first illustration 23E may be that of an apple (FIG. 9A) and a second illustration may be that of just the core of the apple after it is eaten (FIG. 9B).

Figure 10:
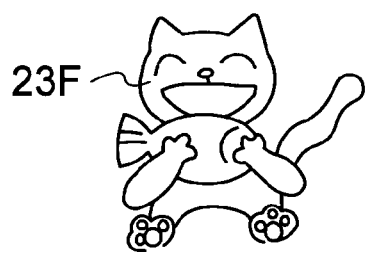
FIG. 10A is a diagram showing a first illustration of a diaper according to an eighth modification example of the present invention.
FIG. 10B is a diagram showing a second illustration of the diaper according to the abovementioned modification example.
Figure 10:
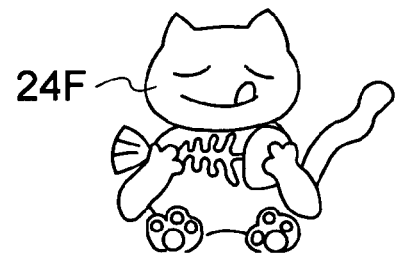

A change of expression and an irreversible transition in time may also be expressed. To be specific, a first illustration 23F may be that of a cat (character) that is happily holding a fish in its hands (FIG. 10A) and a second illustration 24F may be that of the cat who is satisfied after eating the fish and is holding the bones of the fish in its hands (FIG. 10B).

Figure 11:
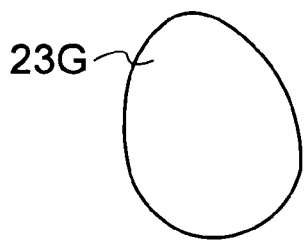
FIG. 11A is a diagram showing a first illustration of a diaper according to a ninth modification example of the present invention.
FIG. 11B is a diagram showing a second illustration of the diaper according to the abovementioned modification example.
Figure 11:
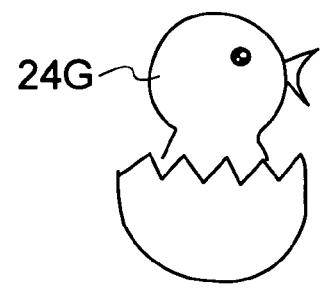
Figure 12:
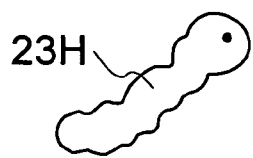
FIG. 12A is a diagram showing a first illustration of a diaper according to a tenth modification example of the present invention.
FIG. 12B is a diagram showing a second illustration of the diaper according to the abovementioned modification example.
Figure 12:
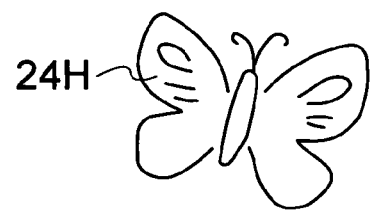
Figure 13:
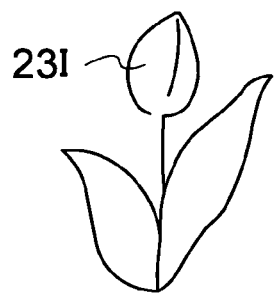
FIG. 13A is a diagram showing a first illustration of a diaper according to an eleventh modification example of the present invention.
FIG. 13B is a diagram showing a second illustration of the diaper according to the abovementioned modification example.
Figure 13:
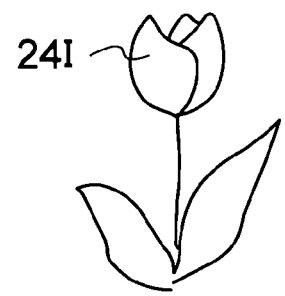

Also, a growth process may be expressed. To be specific, a first illustration 23G may be that of a chicken egg (FIG. 11A) and a second illustration 24G may be that of a chick that shows its face from the egg upon cracking of the egg (FIG. 11B). Or a first illustration 23H may be that of a larva (FIG. 12A) and second illustration 24H may be that of a butterfly (FIG. 12B). Also, a first illustration 23I may be that of a tulip in the bud state (FIG. 13A) and a second illustration 24I may be that of the tulip in bloom (FIG. 13B).

EXAMPLES AND COMPARATIVE EXAMPLES

<Explanation of Interaction Value>

Communications between a diaper exchanger and an infant were evaluated using diapers of the above-described embodiments. Here, in order to evaluate communications in a quantitative manner, an index called an interaction value was used.

The interaction value is expressed by the following equation.

(Interaction value)=(Exchanger approach value)+(Infant response value)

$$(\text{Exchanger approach value}) = \sum_{\text{Start of diaper exchange}}^{\text{End of diaper exchange}} ((\text{Exchanger signal value}) \times (\text{Duration (seconds)})) \quad [\text{Eq. 1}]$$

$$(\text{Infant response value}) = \sum_{\text{Start of diaper exchange}}^{\text{End of diaper exchange}} ((\text{Infant signal value}) \times (\text{Duration (seconds)})) \quad [\text{Eq. 2}]$$

(Positive action value)=Positive element of (Exchanger approach value)+Positive element of (Infant response value)

Here, the "exchanger signal value" refers to all approaches, including crying, laughing, emitting a sound, etc., made by the exchanger to transmit the exchanger's own thought to the infant.

This "exchanger signal value" is deemed to be positive when it accompanies a positive emotion, such as joy, pleasure, etc., and is deemed to be negative when it accompanies a negative emotion, such as discomfort, pain, etc.

The "infant signal value" refers to all approaches, including crying, laughing, emitting a sound, etc., made by the infant to transmit the infant's own thought to the exchanger in response to an approach made by the exchanger to the infant.

This "infant signal value" is deemed to be positive when it accompanies a positive emotion, such as joy, pleasure, etc., and is deemed to be negative when it accompanies a negative emotion, such as discomfort, pain, etc. To be specific, cases where the infant signal value is positive include cases where the infant laughs, emits a sound cheerfully, holds an object, moves towards the exchanger on his/her own, etc. On the other hand, cases where the infant signal value is negative include cases where the infant cries, escapes, becomes angry, struggles, etc.

The period from the "start of diaper exchange" to the "end of diaper exchange" refers to the period from the preparation of a new diaper to the guiding of the infant, removing of the diaper that the infant is already wearing, the washing of the infant's groin and putting of the new diaper, and disposal of the removed diaper.

A higher exchanger approach value signifies that the exchanger approached the child more and a higher infant response value signifies that the infant responded more to the exchanger's approach. A higher positive action value signifies that good communication was carried out more often between the exchanger and the infant. An interaction value of higher positive value signifies that in total, good communication was carried out between the exchanger and the infant.

For example, in a case where a situation in which an infant, who cries and escapes even when guided by the mother, is held down by a mother lasts for 30 seconds, a situation in which the infant laughs while being exchanged to a new diaper and the mother talks to the infant lasts for 20 seconds, and a situation in which the infant says "dada" cheerfully while the mother is throwing the diaper away lasts for 10 seconds, the above values will be as follows:

(Exchanger approach value)=(−1)×30+(+1)×20=−10

(Infant response value)=(−1)×30+(+1)×20+(+1)×10=0

(Positive action value)=20+30=50

(Interaction value)=(−2)×30+(+2)×20+(+1)×10=−10

Examination of Examples and Comparative Examples

The examples and comparative examples were examined using the above-described "interaction value."

Figure 14:
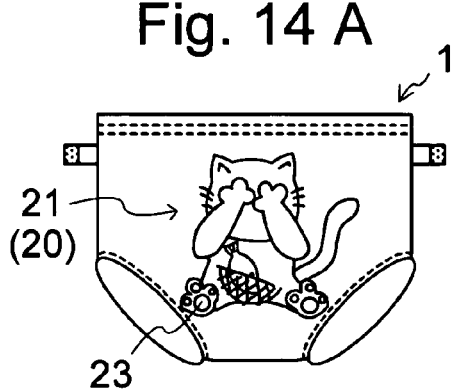
FIG. 14A is a front view of a diaper according to example 1 of the present invention.
FIG. 14B is a rear view of the diaper according to the abovementioned example.
Figure 14:
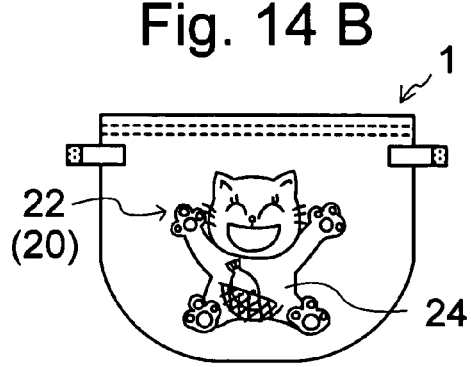

As shown in FIGS. 14A and 14B, with Example 1, a first illustration displaying part 21 and a second illustration displaying part 22 are provided and a behavior of the same character is expressed by a first illustration 23 and a second illustration 24.

Figure 15:
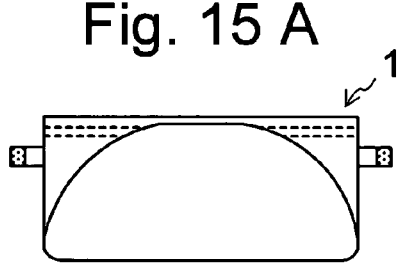
FIG. 15A is a front view of a diaper according to example 2 of the present invention.
FIG. 15B is a rear view of the diaper according to the abovementioned example.
Figure 15:
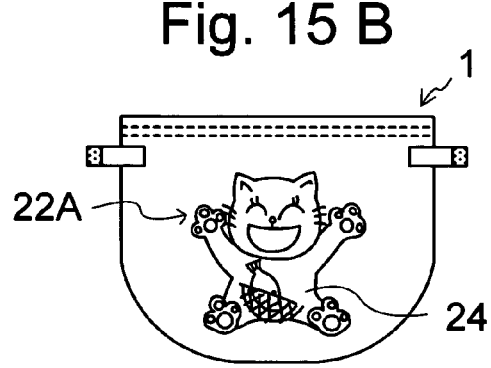

As shown in FIGS. 15A and 15B, with Example 2, only a second illustration displaying part 22A is provided and diaper 1 is folded in half to hide second illustration displaying part 22A so that when diaper 1 is opened, second illustration displaying part 22A becomes exposed.

Figure 16:
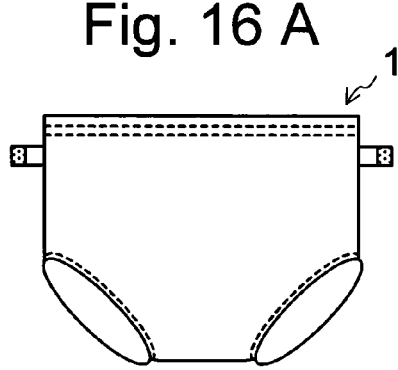
FIG. 16A is a front view of a diaper according to comparative example 1 of the present invention.
FIG. 16B is a rear view of the diaper according to the abovementioned comparative example.
Figure 16:
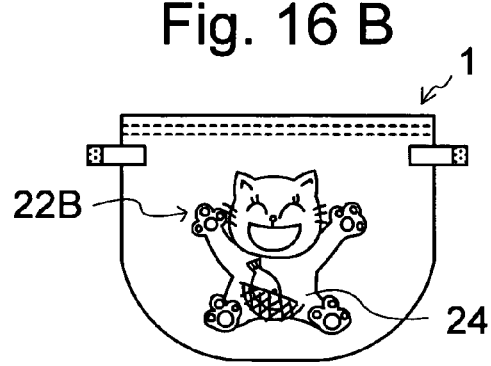

With Comparative Example 1, only a second illustration displaying part 22B is provided as shown in FIGS. 16A and 16B.

Figure 17:
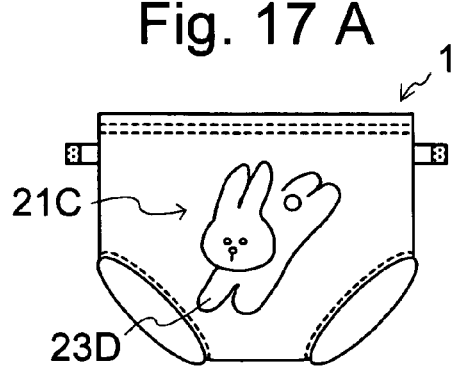
FIG. 17A is a front view of a diaper according to comparative 2 example of the present invention.
FIG. 17B is a rear view of the diaper according to the abovementioned comparative example.
Figure 17:
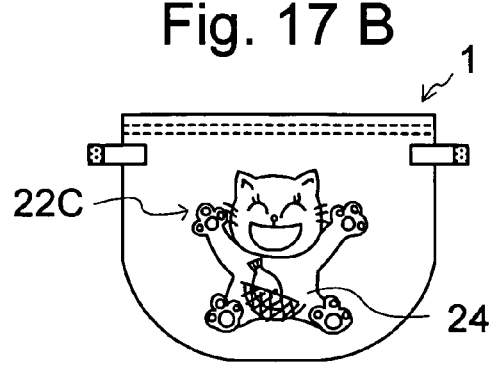

As shown in FIGS. 17A and 17B, with Comparative Example 2, a first illustration displaying part 21C and a second illustration displaying part 22C are provided and different characters are expressed by a first illustration 23D and a second illustration 24.

The above diapers were experimented with infants of the following ages in months as subjects and their mothers as diaper exchangers. The correspondence between the ages in months of the subjects and the age-in-months ranges to which the subjects belong are shown in the Table below.

TABLE 1

| Age in months of subject | Age-in-months range to which subject belongs |
|---|---|
| 9 months age | 6 months or more and less than 12 months from birth |
| 17 months age | 12 months or more and less than 18 |

TABLE 1-continued

| Age in months of subject | Age-in-months range to which subject belongs |
|---|---|
| 19 months age | 18 months or more and less than 24 months from birth |
| 31 months age | 24 months or more and less than 36 months from birth |

The experiment results are shown in the following Table.

TABLE 2

| Age-in-months range | Example 1 | Example 2 | Comparative Example 1 | Comparative Example 2 |
|---|---|---|---|---|
| Exchanger approach value | | | | |
| 6 months or more and less than 12 months from birth | 20 | 20 | 10 | 10 |
| 12 months or more and less than 18 months from birth | 30 | 40 | 10 | 9 |
| 18 months or more and less than 24 months from birth | 50 | 15 | 10 | 20 |
| 24 months or more and less than 36 months from birth | 25 | 10 | 7 | 15 |
| Infant response value | | | | |
| 6 months or more and less than 12 months from birth | 10 | 30 | 0 | 5 |
| 12 months or more and less than 18 months from birth | 40 | 140 | 0 | 3 |
| 18 months or more and less than 24 months from birth | 100 | 45 | 5 | 15 |
| 24 months or more and less than 36 months from birth | 15 | 15 | 4 | 5 |
| Positive action value | | | | |
| 6 months or more and less than 12 months from birth | 30 | 50 | 10 | 15 |
| 12 months or more and less than 18 months from birth | 70 | 180 | 10 | 12 |
| 18 months or more and less than 24 months from birth | 150 | 60 | 15 | 35 |
| 24 months or more and less than 36 months from birth | 40 | 25 | 11 | 20 |
| Interaction value | | | | |
| 6 months or more and less than 12 months from birth | 40 | 80 | 10 | 20 |
| 12 months or more and less than 18 months from birth | 110 | 320 | 10 | 15 |
| 18 months or more and less than 24 months from birth | 250 | 105 | 20 | 50 |
| 24 months or more and less than 36 months from birth | 55 | 40 | 15 | 25 |

The experiments show that with Examples 1 and 2, the exchanger approach value, infant response value, positive action value, and interaction value are higher than those of Comparative (prior art) Examples 1 and 2. The experiments also show that Example 1 provides a high exchanger approach value, infant response value, positive action value, and interaction value for high-month-age infants and Example 2 provides high values of the above for low-month-age infants.

It has thus become clear that low-month-age infants prefer simple movements and high-month-age infants show an interest in the movements of a character itself.

The present invention's method for determining illustrations for a diaper provides the following effects.

An illustration of an illustration displaying part is determined in accordance with the age in months of an infant. The illustration can thereby arouse interest of an infant definitely since the object of interest of an infant depends on his/her age in months. An infant can thus be made to calm down during diaper exchange and the labor of diaper exchange can be alleviated.

What is claimed is:

1. A method of determining effectiveness of an illustration for a diaper during a diaper changing process,
   said diaper comprising:
      a main body, for being fitted onto a body of an infant,
      a first illustration displaying part, provided on the main body, for displaying a first illustration, wherein said illustration is determined based on the age in months of the infant, and
      a second illustration display part displaying a second illustration,
      wherein
      said first illustration and said second illustration express a change of a behavior of a character, an irreversible transition in time, a change near the hands of a character, a change of scene, a movement of a character, a change of expression, or an irreversible transition in time and a growth process, and said first illustration and said second illustration are mutually relevant or integrated as a whole in terms of shape, pattern, color, concept, or combination thereof;
   said method comprising the steps of:
   (a) during the diaper changing process and while showing at least one of the first and second illustrations to the infant whose diaper is to be changed,
      (a1) monitoring signals made by an exchanger and the infant, and
      (a2) measuring the duration of each said signal;
   (b) calculating an exchanger approach value by
      (b1) for each signal made by the exchanger and indicative of the exchanger's positive emotion, calculating an exchanger positive time value as a product of the duration of said signal multiplied by a positive exchanger signal value,
      (b2) for each signal made by the exchanger and indicative of the exchanger's negative emotion, calculating an exchanger negative time value as a product of the duration of said signal multiplied by a negative exchanger signal value, and
      (b3) calculating the exchanger approach value as a sum of said exchanger positive and negative time values;
   (c) calculating an infant response value by
      (c1) for each signal made by the infant and indicative of the Infant's positive emotion, calculating an infant positive time value as a product of the duration of said signal multiplied by a positive infant signal value
      (c2) for each signal made by the infant and indicative of the Infant's negative emotion, calculating an infant negative time value as a product of the duration of said signal multiplied by a negative infant signal value and (c3) calculating the infant response value as a sum of said infant positive and negative time values:
(d) calculating a positive action value as a sum of the exchanger and infant positive time values:
(e) calculating an interaction value as a sum of the exchanger approach value and the infant response value: and
(f) evaluating the effectiveness of said at least one of the first and second illustrations based on at least one of the positive action value and the interaction value.

2. The method of claim 1, wherein in step (a), the first and second illustrations are alternatively shown to the infant.

3. The method of claim 2, wherein the positive emotion is determined by joy or pleasure expressed by the exchanger or infant, and the negative emotion is determined by discomfort or pain expressed by the exchanger or infant.

4. The method of claim 1, wherein the positive emotion is determined by joy or pleasure expressed by the exchanger or infant, and the negative emotion is determined by discomfort or pain expressed by the exchanger or infant.

* * * * *